(12) United States Patent
Barbiaux et al.

(10) Patent No.: US 11,451,567 B2
(45) Date of Patent: Sep. 20, 2022

(54) SYSTEMS AND METHODS FOR PROVIDING SECURE REMOTE DATA TRANSFER FOR MEDICAL DEVICES

(71) Applicant: GE Precision Healthcare LLC, Milwaukee, WI (US)

(72) Inventors: William Barbiaux, Waukesha, WI (US); Michael Walls, West Bend, WI (US); Nathan Davis, Delafield, WI (US)

(73) Assignee: GE Precision Healthcare LLC, Milwaukee, WI (US)

( * ) Notice: Subject to any disclaimer, the term of this patent is extended or adjusted under 35 U.S.C. 154(b) by 182 days.

(21) Appl. No.: 16/556,079

(22) Filed: Aug. 29, 2019

(65) Prior Publication Data

US 2020/0076844 A1 Mar. 5, 2020

Related U.S. Application Data

(60) Provisional application No. 62/725,923, filed on Aug. 31, 2018.

(51) Int. Cl.
*H04L 9/40* (2022.01)
*H04W 12/00* (2021.01)
*H04L 12/46* (2006.01)
*G16H 10/60* (2018.01)

(52) U.S. Cl.
CPC ......... *H04L 63/1425* (2013.01); *G16H 10/60* (2018.01); *H04L 12/4683* (2013.01); *H04L 63/1416* (2013.01); *H04L 63/1441* (2013.01); *H04W 12/009* (2019.01)

(58) Field of Classification Search
CPC ............ H04L 63/1425; H04L 63/1416; H04L 63/1441; H04W 12/009
USPC ......................................................... 726/23
See application file for complete search history.

(56) References Cited

U.S. PATENT DOCUMENTS

| 4,453,221 A | * | 6/1984 | Davis | G05B 19/4163 700/86 |
|---|---|---|---|---|
| 6,377,162 B1 | * | 4/2002 | Delestienne | G16Z 99/00 340/286.07 |
| 9,716,724 B1 | * | 7/2017 | Chennuru | H04L 63/08 |
| 2002/0186683 A1 | * | 12/2002 | Buck | H04L 69/329 370/352 |
| 2004/0167465 A1 | * | 8/2004 | Mihai | A61B 5/411 604/67 |
| 2004/0172300 A1 | * | 9/2004 | Mihai | G16H 40/67 705/2 |
| 2004/0172301 A1 | * | 9/2004 | Mihai | A61B 5/0002 705/2 |
| 2004/0172302 A1 | * | 9/2004 | Martucci | A61B 5/4839 705/2 |

(Continued)

*Primary Examiner* — Dant B Shaifer Harriman
(74) *Attorney, Agent, or Firm* — McCoy Russell LLP

(57) ABSTRACT

Methods and systems are provided for providing a secure connection to a medical device for remote servicing of the medical device. In one embodiment, a computing device is in communication with a medical device, the computing device comprising non-transitory memory including executable instructions for: communicating with the medical device via a first protocol; and communicating with a remote computing device via an encrypted, second protocol. The computing device also includes a processor for executing said executable instructions.

14 Claims, 6 Drawing Sheets

(56) References Cited

U.S. PATENT DOCUMENTS

| | | | | |
|---|---|---|---|---|
| 2004/0176667 | A1* | 9/2004 | Mihai | G16H 40/67 600/300 |
| 2005/0055242 | A1* | 3/2005 | Bello | G16H 20/17 705/2 |
| 2005/0065817 | A1* | 3/2005 | Mihai | A61B 5/411 705/2 |
| 2006/0193437 | A1* | 8/2006 | Boeing | A61B 6/465 378/115 |
| 2008/0040157 | A1* | 2/2008 | Saunders | G06Q 10/10 705/3 |
| 2009/0113064 | A1* | 4/2009 | Yamaki | H04L 69/08 709/230 |
| 2011/0087237 | A1* | 4/2011 | Viswanathan | A61B 34/70 380/42 |
| 2013/0304489 | A1* | 11/2013 | Miller | G06Q 10/20 705/2 |
| 2014/0288947 | A1* | 9/2014 | Simpson | G16H 10/60 705/2 |
| 2015/0081579 | A1* | 3/2015 | Brown | H04W 4/02 705/325 |
| 2019/0130075 | A1* | 5/2019 | Henein | G06F 21/577 |
| 2019/0190952 | A1* | 6/2019 | Cherry | H04L 63/1491 |
| 2020/0388390 | A1* | 12/2020 | Singh | H04L 63/20 |
| 2022/0054008 | A1* | 2/2022 | Venkatraman | A61B 5/0004 |

* cited by examiner

SYSTEMS AND METHODS FOR PROVIDING SECURE REMOTE DATA TRANSFER FOR MEDICAL DEVICES

CROSS REFERENCE TO RELATED APPLICATIONS

The present application claims priority to U.S. Provisional Application No. 62/725,923, titled "SYSTEMS AND METHODS FOR PROVIDING SECURE REMOTE DATA TRANSFER FOR MEDICAL DEVICES", and filed on Aug. 31, 2018. The entire contents of the above-identified application are hereby incorporated by reference for all purposes.

FIELD

Embodiments of the subject matter disclosed herein relate to the security of medical devices and to the configurability of aftermarket computing devices for medical devices.

BACKGROUND

Hospital medical devices such as CT scanners, MRI machines, and anesthesia machines, may need to be periodically serviced by a remote engineer. To access the medical device remotely, an engineer may establish a connection with the hospital's private network via a secure VPN protocol. The engineer may begin servicing the medical device via this secure VPN connection, over the hospital's network.

However, although the engineer's connection to the device may be secured (encrypted) between the engineer's remote computer and the hospital's private network, the connection may not be secured (encrypted) between the hospital's private network and the medical device. Thus, because the medical device may contain unsecured, open ports, traffic over the hospital's network, including sensitive information such as the remote engineer's passwords and/or login information, may be vulnerable to exposure and discovery by third parties located at the hospital.

Many medical devices may include supplemental, external computing systems to aid in certain processing tasks, such as image post-processing, when the processing power of the medical device itself is inadequate. For example, aftermarket computing devices may be coupled to the medical devices to extend the processing capabilities of the medical devices. Although purposed for providing additional processing power, there is an opportunity for these aftermarket computing devices to also increase the security of these medical devices by closing/securing open ports on the medical device. However, configuring these aftermarket computing devices to act as a firewall for these medical devices may be difficult because the medical devices themselves, and the systems in which they are integrated, may be highly specialized and the protocols they use may be highly varied and particular. Further, the types of protocols and medical devices may vary greatly from hospital to hospital. Thus, building the software for these aftermarket computing devices may be time consuming, because the software may need to be individually tailored for each medical device and/or hospital network.

For example, the device must use the medical device's protocol to communicate with the medical device while simultaneously using a more secure, encrypted security protocol to communicate with the remote computer. Even just identifying the correct protocol to use to communicate with the medical device may be difficult since the protocols used by different medical devices may be vast and highly varied. Further, it may be difficult to develop appropriate screening rules for the firewall so that important hospital information, such as clinical data, is not blocked by the device's firewall since the protocols used to communicate such clinical data may be very highly varied and innumerable among hospitals.

BRIEF DESCRIPTION

In one embodiment, a computing device in communication with a medical device comprises non-transitory memory including executable instructions for: communicating with the medical device via a first protocol, and communicating with a remote computing device via an encrypted, second protocol; wherein the computing device further comprises a processor for executing said executable instructions. In this way, a medical device may be serviced more securely via an encrypted connection between the computing device and a remote device, minimizing the risk of exposure to third parties.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below.

DETAILED DESCRIPTION

The following description relates to various embodiments of secure, remote servicing of medical devices. In particular, systems and methods are provided for remotely and securely accessing a hospital medical device via an aftermarket computing device, herein referred to as an edge computing system (ECS) or edge mini device. In a conventional prior art system, such as the system depicted in FIG. 1A, the ECS is not included in the system, and a remote user's connection to the medical device is only encrypted between the remote user's computer and the hospital network. However, the remote user's connection is not encrypted between the hospital network and the medical device, thus making sensitive information conveyed over this connection vulnerable to exposure and discovery by third parties on the hospital network.

Figure 1A:
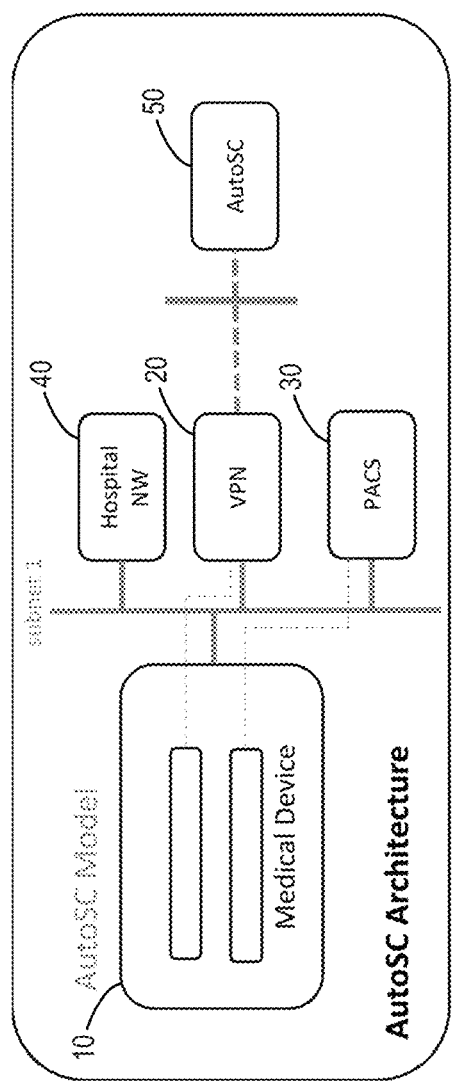
FIG. 1A shows a block schematic diagram of a prior art system for servicing a medical device according to an embodiment.
Figure 1B:
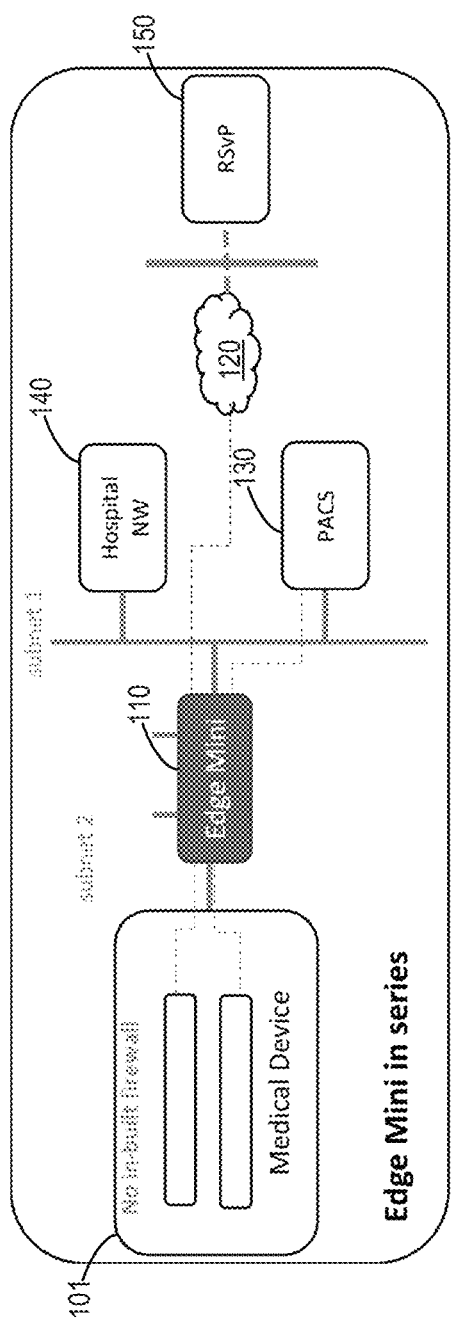
FIG. 1B shows a block schematic diagram of a more secure example system for servicing a medical device according to an embodiment.
Figure 1C:
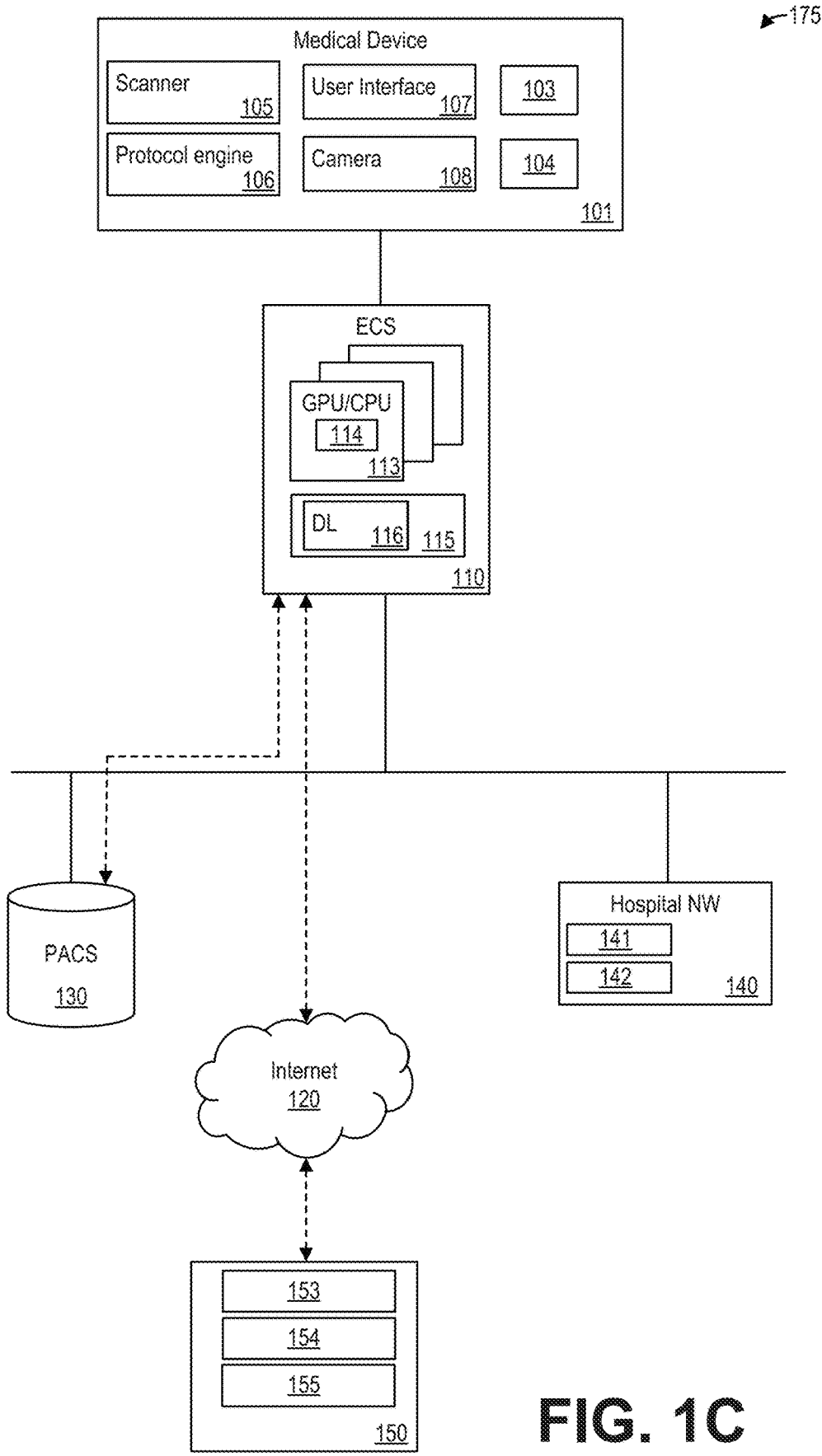
FIG. 1C shows a more detailed block schematic diagram of the example system of FIG. 1B according to an embodiment.

However, as shown in FIGS. 1B and 1C, the secureness of this connection between the remote user's computer and the medical device may be increased by including the ECS proximate to the medical device, between the medical device and the hospital network. In this way, the connection with the remote user's computer may be encrypted and secured all the way from the remote user's computer to the ECS. Thus, the ECS includes a firewall that closes/secures open ports on the medical device and makes it more difficult for potential hackers to access sensitive information, while still allowing clinical data to pass through. Further, the ECS may be configured to communicate with the remote user's computer using a more secure protocol than a traditional VPN protocol while still being able to communicate with the medical device via the medical device's own service protocols. The ECS therefore acts as a translator, converting between the medical device's service protocols, and the more secure remote access protocols, as depicted in the example method of FIG. 2. Additional information relating to the configurability and interpretive functionality of the ECS is depicted in the example method of FIG. 3. FIG. 4 describes an example method for remotely servicing the medical device via the ECS.

The ECS is connected to a medical device, such as a scanner, anesthesia delivery machine, incubator, and so forth, for increasing the processing power of the medical device to aid in various tasks such as image post-processing, data processing and analysis, execution of machine learning models, and the like. The ECS includes CPUs/GPUs running one or more virtual machines (VMs) configured for different types of tasks. Data is streamed in real-time from the scanner to the ECS which processes the data (in image and/or projection space) and returns the results.

The ECS also acts as a firewall, filtering traffic into the medical device and securing open ports on the medical device. In particular, the ECS blocks and/or screens incoming traffic, while allowing clinical data to be transmitted freely between the medical device and the hospital network. Further, the ECS may enable one or more remote users to establish an encrypted connection with the ECS, to more securely service and access the medical device.

In an example, the ECS may include detailed device communication models (e.g., models of the medical device's network protocols) stored in memory of the ECS. These models may be used to configure firewalls and determine protocol translations. The developed model or models may be applied to multiple ECS devices that are connected to the same "family" of medical device (e.g., all MRI scanners of a particular type, line, or model may be represented by one network model).

FIG. 1A shows a block schematic diagram of an example prior art system 100 (also referred to herein as the "AutoSC Model"), for servicing a medical device 10, where an ECS is not included in the system. In the prior art system 100, an AutoSC agent 50 services a medical device 10 via a virtual private network (VPN) connection 20. Through the VPN connection 20, the AutoSC agent 50 gains access to a hospital network 40 on which the medical device 10 is included. However, the connection is only encrypted between the AutoSC agent 50 and the hospital network 40. The connection is not encrypted between the hospital network 40 and the medical device, making the connection vulnerable to potential hackers located on the hospital network 40. The medical device 10 is connected to a picture archiving and communication system (PACS) 30 for sending clinical data such as patient image data from a scan performed by the medical device 10 to the PACS 30. The PACS 30 is a non-limiting example of networked device/system to which the medial device 10 may be coupled, and other devices/systems are possible, such as an electronic medical records (EMR) database, a radiology information system (RIS), etc.

FIGS. 1B and 1C depict an example system 175 according to an embodiment of the present disclosure for providing more secure remote servicing of a medical device 101 with an edge computing system 110 (also referred to herein as the "Edge Mini 110"). FIG. 1C merely shows a more detailed the components of system 175, and as such, FIGS. 1B and 1C will be described together herein. The medical device 101 may comprise any suitable medical device, including but not limited to medical therapy devices (such as anesthesia delivery machines), mother-infant care devices (such as an infant incubator), patient monitoring devices (such as diagnostic cardiology/ECGs), and non-invasive imaging systems (such as a computed tomography (CT) imaging system, a positron emission tomography (PET) imaging system, a magnetic resonance (MR) imaging system, an X-ray imaging system, an ultrasound system, and combinations thereof (e.g., a multi-modality imaging system such as a PET/CT or PET/MR imaging system)). The example medical device provided in FIG. 1C is an imaging device, but it is to be understood that systems and methods described herein likewise apply to other types of medical devices.

The medical device 101 includes a processor 103 and non-transitory memory 104. One or more methods may be implemented as executable instructions in the non-transitory memory 104 that when executed by the processor 103 cause the processor 103 to perform various actions.

The medical device 101 further comprises a scanner 105 for scanning a subject such as a patient to acquire imaging data. Depending on the type of medical device 101, the scanner 105 may comprise multiple components necessary for scanning the subject. For example, if the medical device 101 comprises a CT imaging system, the scanner 105 may comprise a CT tube and a detector array, as well as various components for controlling the CT tube and the detector array. As another example, if the medical device 101 comprises an ultrasound imaging system, the scanner 105 may comprise an ultrasound transducer. Thus, the term "scanner" as used herein refers to the components of the imaging system which are used and controlled to perform a scan of a subject. In examples where the medical device is not an imaging device, the scanner may not be part of the medical device. Instead, the medical device may include one or more other patient monitoring/patient interfacing components, such as a vaporizer (in the case of an anesthesia delivery machine), ECG leads, an incubator, etc.

The type of imaging data acquired by the scanner 105 also depends on the type of medical device 101. For example, if the medical device 101 comprises a CT imaging system, the imaging data acquired by the scanner 105 may comprise projection data. Similarly, if the medical device 101 comprises an ultrasound imaging system, the imaging data acquired by the scanner 105 may comprise analog and/or digital echoes of ultrasonic waves emitted into the subject by the ultrasound transducer. When the medical device is not an imaging device, data obtained by the medical device may include ECG data, determined anesthesia concentration and measured patient breathing parameters, patient temperature, and so forth.

In some examples, the medical device 101 includes a protocol engine 106 for automatically selecting and adjusting a scan protocol for scanning a subject. A scan protocol selected by protocol engine 106 prescribes a variety of settings for controlling the scanner 105 during a scan of the subject. As discussed further herein, protocol engine 106 may select or determine a scan protocol based on an indicated primary task. Although the protocol engine 106 is depicted as a separate component from the non-transitory memory 104, it should be understood that in some examples the protocol engine 106 may comprise a software module stored in non-transitory memory 104 as executable instructions that when executed by the processor 103 causes the processor 103 to select and adjust a scan protocol.

The medical device 101 further comprises a user interface 107 configured to receive input from an operator of the medical device 101 as well as display information to the operator. To that end, user interface 107 may comprise one or more of an input device, including but not limited to a keyboard, a mouse, a touchscreen device, a microphone, and so on, and an output device, including but not limited to a display device, a printer, and so on.

In some examples, the medical device 101 further comprises a camera 108 for assisting with the automatic positioning of the subject within the imaging system. For example, the camera 108 may capture live images of the subject within the imaging system, while the processor 103 determines a position of the subject within the imaging system based on the live images. The processor 103 may then control a table motor controller, for example, to adjust the position of a table upon which the subject is resting in order to position at least a region of interest (ROI) of the subject within the imaging system. Furthermore, in some examples, a scan range may be at least approximately determined based on the live images captured by the camera 108.

The medical device 101 has no built-in firewall. However, the system 100 further comprises an edge computing system (ECS) 110 that serves as a firewall for the medical device 101. The ECS 110 is communicatively coupled to the medical device 101 via a wired or wireless connection. The ECS 110 also serves as a source of additional processing power for the medical device 101. For example, the ECS 110 may perform various post-processing and/or deep learning techniques to improve the accuracy of image data acquired from the medical device 101. In examples where the ECS is coupled to a medical device that is not an imaging system, the ECS may perform other processing tasks, such as deep learning techniques to determine when to wean an infant from an incubator, processing of medical device data (e.g., ECG data), and so forth. The ECS 110 comprises a plurality of processors 113 running one or more virtual machines (VMs) 114 configured for different types of tasks. The plurality of processors 113 comprise one or more graphics processing units (GPUs) and/or one or more central processing units (CPUs). The ECS 110 further comprises non-transitory memory 115 storing executable instructions that may be executed by one or more of the plurality of processors 113. One or more methods described herein may be implemented as executable instructions in the non-transitory memory 115 that when executed by the processors 113 cause the processors 113 to perform various actions. Such methods are described further herein with regard to FIGS. 2-3. The non-transitory memory 115 may further include a deep learning (DL) model 116 that may be executed by a virtual machine 114 of the plurality of processors 113.

In some examples, the ECS 110 may be an aftermarket device that is added to the system 100 to extend the processing capabilities of the medical device 101. The ECS 110 may also provide additional security protection by acting as a firewall for the medical device 101, securing open ports on the medical device 101 and filtering incoming traffic. Thus, the ECS 110 may comprise a router and/or firewall.

The ECS 110 may communicate with the medical device 101 using one or more medical device protocols. The one or more medical device protocols may include standard network protocols such as Telnet, or the medical device protocols may include proprietary protocols that are specific to the equipment manufacturer of the medical device. That is, the ECS 110 may include executable instructions stored in the non-transitory memory 115 for using and understanding the protocol used by the medical device 101. As described in greater detail below with reference to FIG. 3, the ECS 110 may additionally include instructions for more efficiently configuring the ECS 110 to communicate with the medical device 101. In particular, the ECS 110 may include instructions stored in non-transitory memory 115 for determining the particular medical device protocol used by the medical device 101. Further, the ECS 110 may include instructions for more efficiently establishing the filtering rules of the firewall of the ECS 110.

In some examples, the system 100 further comprises one or more external databases 130 that the medical device 101 and the ECS 110 may be communicatively coupled to via a private, hospital network 140. The one or more external databases 130 store clinical data and may comprise, as exemplary and non-limiting examples, one or more of a picture archiving and communication system (PACS), hospital information system (HIS), a radiology information system (RIS), and an electronic medical record (EMR) system. The medical device 101 and/or the ECS 110 may retrieve clinical data from the external databases 130, such as subject metadata describing or relating to a particular subject to be scanned, which may include an EMR for the subject. Further, the ECS 110 may allow image data and/or other data created by the medical device 101 to be transmitted to the external databases 130 and stored on the databases 130.

The clinical data may include subject metadata, clinical and/or administrative data communicated via HL7 standards, and/or medical imaging data communicated via DICOM standards to convey medical records and images, respectively, and may also include common IP protocols such as SSH. The clinical data may be communicated on network 140 using one or more clinical data protocols. Thus, the ECS 110 understands the clinical data protocols, does not interfere with the clinical data protocols, and thereby enables the clinical data to flow freely between the hospital network 140 and the medical device 101.

Further, the ECS may encrypt the data communicated between the ECS 110 and the external databases 130 using one or more encryption methods. That is, the ECS 110 may include one or more encryption methods stored in non-transitory memory 115, which may be executed by the processors 113 to encrypt the data transferred between the ECS 110 and the external databases 130.

The ECS 110 and the external databases 130 may be communicatively coupled via the private, hospital network 140. In particular, the hospital network 140 may include one or more network devices, such as one or more routers 141, one or more modems 142, switches, hubs, and/or other network intermediary devices that serve as network access points, thereby communicatively coupling the various devices on the hospital network 140 and providing connectivity to an internet service provider (ISP) to provide access to the Internet 120 for the various devices included on the private hospital network 140. Thus, The ECS 110 may be connected to the Internet 120 via the hospital network 140, in some examples. The hospital network 140 may further include other systems that communicate with the medical device using clinical protocols such as HL7, and may include other medical devices, administrative devices, etc., that do not normally interact with the medical device.

The system 100 may further include a remote computing device 150 (also referred to herein as "RSvP Enterprise 150") such as one or more servers that may be accessed via a desktop computer, laptop, tablet, etc. The remote computing device 150 may include one or more service applications that may be used to monitor, troubleshoot, and/or service the medical device 101. For example, the servicing may comprise proactive monitoring to identify performance issues that may be resolved via the service applications, maintenance prediction to continuously monitor the medical device and forecast maintenance needs, inventory tracking, maintenance compliance, and so forth.

The remote computing device 150 includes a processor 153 for executing stored instructions and non-transitory memory 154 for storing said executable, stored instructions. One or more methods, such as the methods described herein with regards to FIG. 4 may be implemented as executable instructions in the non-transitory memory 154 that when executed by the processor 153 cause the processor 153 to perform various actions. The remote computing device 150 also includes a user interface 155 comprising one or more input devices for receiving various inputs from a user of the remote computing device 150. For example the user interface 155 may include one or more of a keyboard, mouse, display screen, touch screen, etc.

The ECS 110 and remote computing device 150 may communicate over the Internet 120 using one or more protocols. In particular, the ECS 110 and remote computing device 150 may communicate using a remote access protocol such as Telnet. Further, the remote access protocol may be embedded in a security protocol that encrypts the information communicated between the ECS 110 and the remote computing device 150. The ECS 110 and remote computing device 150 therefore include executable software instructions stored in non-transitory memory for understanding and communicating with at least these two types of protocols. In this way, the ECS emulates the service applications on the remote computing device by speaking protocols that the medical device understands and may be insecure/unencrypted, and translates/converts those protocols into more secure means of communication to the actual service applications on the remote computing device.

For example, the remote computing device 150 may include one or more applications that enable remote access of the ECS 110 and medical device 101. In particular, the applications on the remote computing device 150 may include instructions stored in non-transitory memory 154 for using and understanding the one or more remote access protocols and the one or more security protocols. In some examples, the insecure protocol from the medical device may be wrapped in or tunneled through a secure protocol between the ECS and the remote computing device/service applications. In other examples, the ECS may speak an old, insecure protocol to the medical device, and then translate the information and use a different secure protocol to talk with the remote computing device/service applications. For example the one or more remote access protocols may include Telnet, FTP, RDP, VNC, HTTP, SSH, SFTP, X Windows, rexec, and/or proprietary protocols. The security protocol may include one or more of: an HTTPS protocol and TLS protocol.

The ECS 110 also includes instructions stored in non-transitory memory 115 for using and understanding the one or more remote access protocols and one or more security protocols. Additionally, the ECS 110 may include executable instructions stored in non-transitory memory 115 for establishing a connection with the remote computing device 150. Specifically, the ECS 110 may periodically send an outbound encrypted message querying the remote computing device 150 whether it is desired for the remote computing device 150 to log into the ECS 110. For example, the encrypted message may identify the ECS 110 as the device sending the encrypted message, and may include information such as a log file.

The one or more security protocols encrypt the information transferred between the ECS 110 and the remote computing device 150. In this way, information transmitted between the medical device 101 and the remote computing device 150 may be encrypted all the way from the ECS 110 to the remote computing device 150, minimizing the risk of exposure to third parties located on the hospital network 140.

In this way, the ECS may emulate service applications (e.g., running on the remote computing device) to the medical device, translate the received data, and then emulate the medical device to the service applications over secured channels. In doing so, the ECS 110 may act as an interpreter, translating between the medical device protocol and the one or more protocols of the remote computing device 150. Because the ECS 110 can understand and communicate using both the protocols of the medical device 101 and the more secure protocols of the remote computing device 150, the ECS 110 enables a more secure, encrypted connection to be established with the remote computing device 150, without requiring the medical device 101 itself to be updated. Thus, the medical device 101 can use its extant protocol and still communicate with the remote computing device 150 on the more secure encrypted protocols because the ECS 110 can convert between the protocols. Further, the ECS 110 does not interfere with the flow of clinical data on the hospital network 140 and can be seamlessly integrated into the hospital network 140 because its software can efficiently configure and adapt to the medical device 101 and hospital network 140 as described in greater detail below with reference to FIGS. 2-3.

Figure 2:
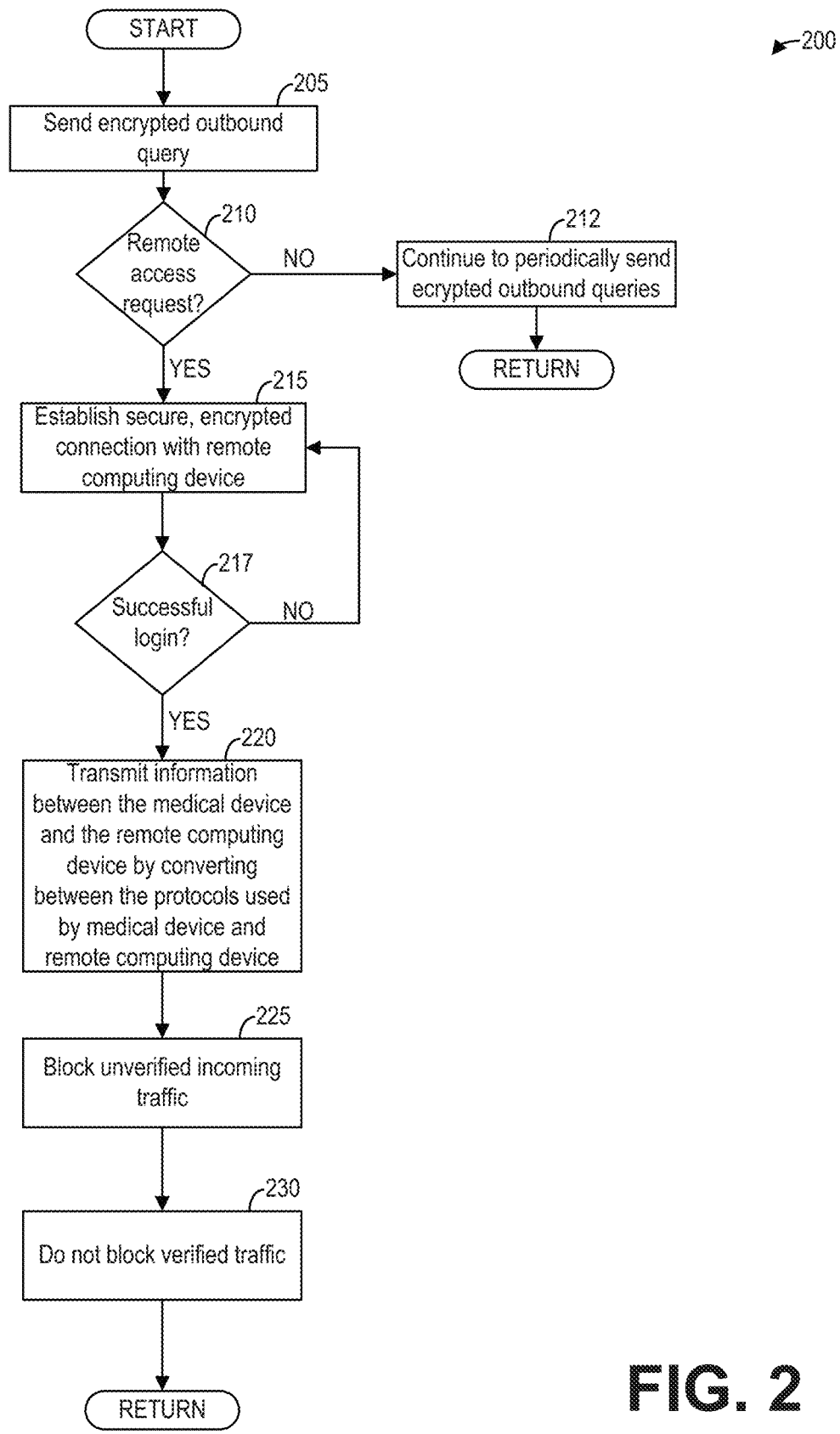
FIG. 2 shows a high-level flowchart illustrating an example method for closing/securing open ports on a medical device and establishing a secure, encrypted remote connection between the medical device and a remote computing device according to an embodiment.
Figure 3:
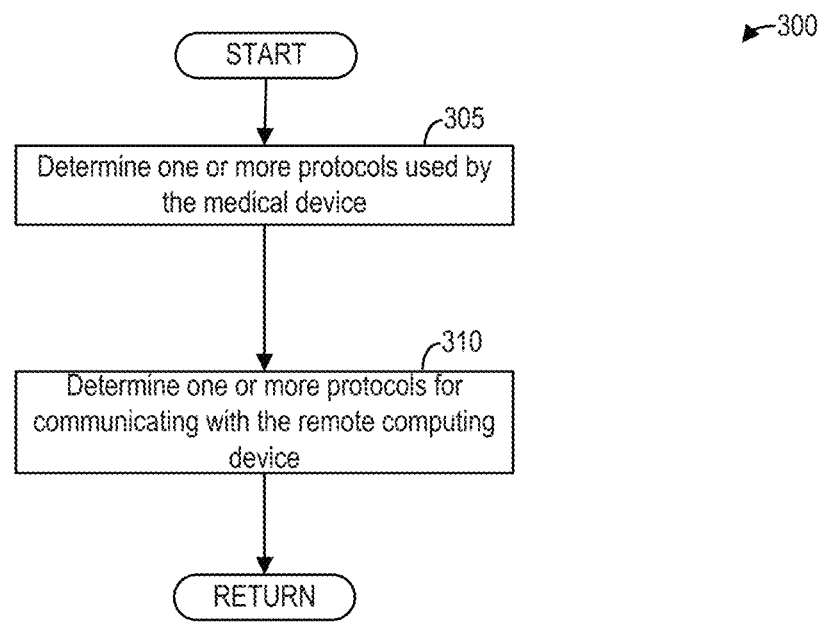
FIG. 3 shows a high-level flowchart illustrating an example method for more efficiently and quickly configuring an aftermarket device's firewall for a given medical device and hospital network according to an embodiment.
Figure 4:
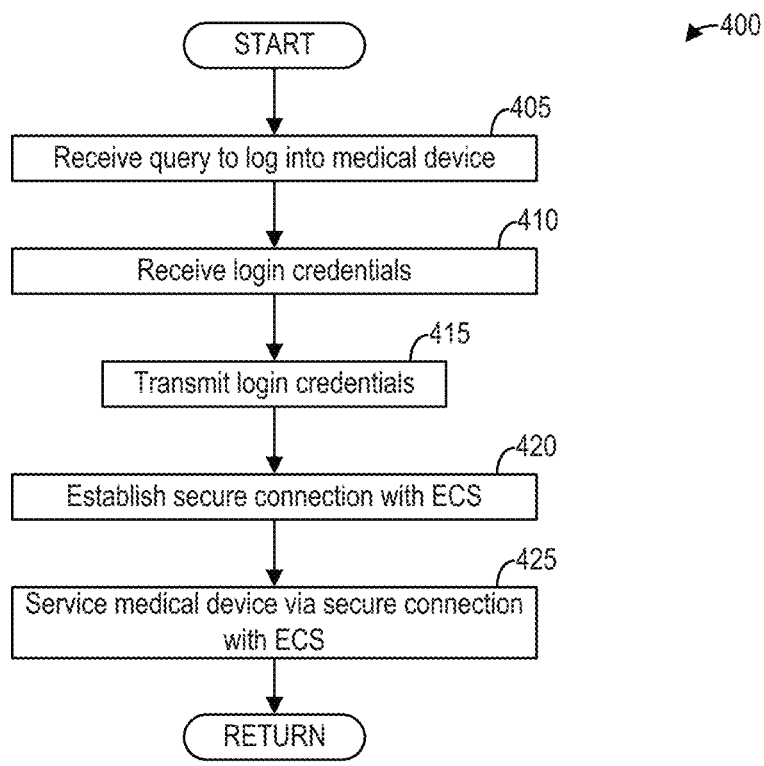
FIG. 4 shows a high-level flowchart illustrating an example method for remotely servicing a medical device using an encrypted connection according to an embodiment.

FIGS. 2 and 3 show example methods that may be employed by the ECS 110 for adapting to the hospital network 140, specifically to the protocols employed by the medical device 101, and for providing a more secure connection between the remote computing device 150 and the medical device 101. The method shown in FIG. 4 may be employed by the remote computing device 150, in conjunction with a user of the remote computing device 150, to remotely access the medical device 101 and service the medical device 101.

FIG. 2 shows a high-level flowchart illustrating an example method 200 for providing a secure, remote connection between a medical device and a remote computing device. In particular, method 200 relates to remotely connecting to a medical device (e.g., medical device 101 described above with respect to FIG. 1C) from a remote computing device (e.g., remote computing device 150 described above with respect to FIG. 1C) to service the medical device. Method 200 is described with regard to the systems and components depicted in FIGS. 1B and 1C and described hereinabove, though it should be appreciated that the method may be implemented with other systems and components without departing from the scope of the present disclosure. Method 200 may be implemented as executable instructions in non-transitory memory 115 of ECS 110 which may be executed by processors 113 of the ECS 110.

Method 200 begins at 205. At 205, method 200 sends an encrypted outbound message querying remote computing device 150 if it is desired for the remote computing device 150 to log into the medical device 101. The encrypted outbound message may include information identifying the ECS 110 as the device sending the message and may be sent using HPPT or TLS security protocols.

Continuing at 210, method 200 determines if a remote access request has been received. For example, the remote access request may be sent from the remote computing device 150 in response to a user of the remote computing device 150 (e.g., a service engineer) entering an input requesting access to the medical device 101.

If a remote access request is not received, then method 200 continues from 210 to 212. At 212, the method 200 comprises continuing to periodically send the encrypted outbound queries to the remote computing device 150. In some examples, the outbound queries may be sent at regular intervals, such as every two minutes, as just one non-limiting example. Method 200 then returns.

However, if there has been a remote access request at 210, then method 200 continues from 210 to 215. At 215, a secure, encrypted connection is established with the remote computing device 150 (e.g., between the remote computing device and the ECS 110). In particular, the method 200 may comprise employing one or more security protocols such as HTTPS or TLS. Thus, at 215, the ECS 110 may communicate with the remote computing device 150 using one or more of the security protocols that encrypt the information being transmitted between the ECS 110 and the remote computing device 150.

At 217, method 200 includes determining if a login has been successful. For example, a successful login may occur when a user on the remote computing device 150 logs into the medical device 101 (e.g., enters correct login credentials) using a remote access application, for example.

If a successful login has not occurred, method 200 returns to 215 and waits for a successful login. If a successful login occurs, method 200 proceeds to 220, to transmit information between the medical device 101 and the remote computing device 150 by converting between the different protocols used by the medical device 101 and the remote computing device 150. In particular, for information sent from the remote computing device 150 to the medical device 101, the method 200 decrypts the encrypted information received from the remote computing device 150. Further, the method 200 translates this information into the protocol of the medical device and then transmits this information to the medical device 101 using the medical device's protocol.

Conversely, when information is being transmitted to the remote computing device 150 from the medical device 101, the method 200 at 220 comprises converting the information received from the medical device 101 from the medical device's protocol into the protocol of the remote computing device 150, encrypting the information using the security protocol, and then transmitting this encrypted information to the remote computing device 150 using one or more of the remote access protocols. For example, the ECS may include network listeners that understand the medical device protocols. The ECS may include instructions stored in non-transitory memory to convert the network traffic to a modern and secure protocol before transmitting the traffic to the remote computing device. Alternatively, the ECS may tunnel the information from the medical device (which is in the medical device's protocol) through the secure protocol between the ECS and the remote computing device. In some examples, the ECS may utilize the capability of the remote computing device to encrypt data as a standard method. Since the remote computing device traffic is already completely encrypted by default, any data flowing to the remote computing device is encrypted. For example, the ECS may use standard TLS encryption protocols to negotiate the correct encryption protocol to use.

At 225, unverified incoming traffic is blocked. The unverified incoming traffic may include any traffic not specifically authorized by the screening rules of the firewall of the ECS 110. For example, the unverified incoming traffic may include unauthorized attempts to access the medical device 101 by third parties located between the ECS 110 and the remote computing device 150. For example, the firewall may be a standard firewall (e.g., Linux iptables) using custom rules to block unwanted traffic and allow traffic that should pass to the medical device.

At 230, verified traffic is not blocked. The verified traffic may include standard medical image/data traffic such as via HL7 and/or DICOM standards, screen control traffic, VNC screen sharing, and/or other possible site specific traffic on a site by site basis. The firewall rules determine what traffic should pass through versus what traffic will not. For example, the protocol under which the traffic is sent may be identified based on the TCP port on which the traffic is received. As examples, TCP port 104 may be used for DICOM traffic, UDP port 2575 may be used for HL7 traffic, etc. The firewall rules may determine that all DICOM, HL7, and other approved clinical traffic may be sent and not blocked. Method 200 then returns.

Thus, a method for establishing a secure connection between a remote computing device and a medical device for servicing of the medical device comprises communicating with the remote computing device using a remote access protocol and an encrypted security protocol, communicating with a medical device using a medical device protocol, and converting between the protocols to enable communication between the medical device and the remote computing device. In this way, a more secure, encrypted connection may be established all the way from the remote computing device to the ECS without having to update the medical device.

However, not all medical devices use the same protocols. That is, different medical devices may contain different protocols for communicating over a network. Further, the protocols used to communicate verified traffic (such as clinical data) may be different depending on the hospital and hospital network. Thus, as described herein below with regard to FIG. 3, the ECS may need to be configured for, and adapt to, each particular hospital network and medical device. The ECS may therefore comprise executable instructions stored in non-transitory memory for more efficiently identifying the particular protocols employed by the medical device and verified traffic on the hospital network, so that the ECS may more quickly adapt to the system.

FIG. 3 shows a high-level flowchart illustrating an example method 300 for configuring an ECS. In particular, method 300 relates to configuring an ECS for the protocols of a given medical device and hospital network. Method 300 is described with regard to the systems and components of FIGS. 1B and 1C, though it should be appreciated that the method may be implemented with other systems and components without departing from the scope of the present disclosure. Method 300 may be implemented as executable instructions in non-transitory memory 115 of ECS 110 and executed by processors 113 of the ECS 110.

Method 300 begins at 305. At 305, method 300 determines the protocol used by the medical device 101. In some examples, the ECS may include one network model saved in memory that specifies the network protocol(s) used by the medical device 101. The network model may be specific to the particular medical device make, model, line, etc. For example, the ECS may be coupled to an MRI machine of a specific manufacturer, year, make, and model, and the network model may specify which protocol(s) that specific MRI machine is adapted to communicate with. In such examples, the ECS may only be configured to translate from the specific protocol(s) to the secure remote access protocol of the remote computing device. However, in other examples, the ECS may include more than one network model saved in memory, and may include a look-up table or other mechanism by which the correct network model may be applied in order to determine which protocol the medical device communicates in, so that information from the medical device may be properly translated. The look-up table may be indexed by medical device parameters (e.g., manufacturer, make, model, year, etc.) so that the network protocol(s) used by the medical device to which the ECS is coupled may be determined.

In an example, a provisioning process may be performed when the ECS is installed. During the provisioning process, a configuration file may be downloaded to the ECS so the ECS knows which protocols to use for the medical device that it is connected to. Alternatively, the ECS may interrogate the medical device to learn which protocols are supported and automatically configure itself appropriately.

At 310, method 300 determines the one or more protocols used for transmitting clinical data on hospital network 140. The protocols used for communicating with the remote computing device may be the same protocols used to communicate with the medical device, e.g., a one to one match with the protocol used to communicate with the medical device. Method 300 then returns.

FIG. 4 shows a high-level flowchart illustrating an example method 400 for remotely servicing a medical device (e.g., medical device 101 described above in FIGS. 1B and 1C) according to an embodiment. In particular, method 400 relates to remotely logging into the medical device, and establishing a secure, encrypted connection between the medical device and a supplemental processing unit coupled to the medical device (e.g., ECS 110 described above in FIGS. 1B and 1C). Method 400 is described with regard to the systems and components of FIGS. 1B and 1C, though it should be appreciated that the method may be implemented with other systems and components without departing from the scope of the present disclosure. Method 400 may be implemented as executable instructions in non-transitory memory 154 of the remote computing device 150 and may be executed by the processor 153 of the remote computing device 150.

Method 400 begins at 405. At 405, a query to log into the medical device 101 from the ECS 110 is received.

At 410, login credentials are received. For example, a user may input their login credentials via the user interface 155. Further, the method 400 at 410 may present a login window to the user responsive to the query received from the ECS 110 and/or in response to a request from the user to log into the medical device 101.

At 415, the login credentials are transmitted to the ECS 110, for example the login credentials may be received by the ECS via the secure connection with the remote computing device. If the login credentials are correct and confirmed by the ECS 110, then the method 400 continues from 415 to 420.

At 420, a secure connection with the ECS 110 is established. As described above in FIG. 2, for example, a secure connection may be established with the ECS 110 via a security protocol that encrypts information sent between the ECS 110 and the remote computing device 150.

At 425, the medical device is serviced via the secure connection with the ECS 110. The servicing may comprise fixing configuration issues, database issues, operating system issues, or other user configuration requests from the customer. Method 400 then returns.

A technical effect of the disclosure is to utilize a supplemental, aftermarket computing device originally purposed for increasing the processing power of the medical device, to additionally provide a firewall for the medical device and provide enhanced security and protection for the medical device when remotely accessing the device. Another technical effect of the disclosure is to increase the configurability and adaptability of the aftermarket computing device so that it can more quickly integrate within the hospital network and more immediately start providing its enhanced security measures without blocking the flow unimpeded within the network.

In one embodiment, a computing device in communication with a medical device comprises non-transitory memory including executable instructions for: communicating with the medical device via a first protocol, and communicating with a remote computing device via an encrypted, second protocol; and a processor for executing said executable instructions.

In a first example of the computing device, the non-transitory memory of the computer device further includes executable instructions for determining firewall screening rules. In a second example of the computing device optionally including the first example, the firewall screening rules comprise rules for categorizing incoming traffic as either verified or unverified traffic. In a third example of the computing device optionally including one or more of the first and second examples, the non-transitory memory of the computing device further includes executable instructions for blocking unverified traffic. In a fourth example of the computing device optionally including one or more of the first through third examples, the non-transitory memory of the computing device further includes executable instructions for permitting verified traffic to pass through the computing device. In a fifth example of the computing device optionally including one or more of the first through fourth examples, the non-transitory memory of the computing device further includes executable instructions for identifying the first protocol from a list of protocols. In a sixth example of the computing device optionally including one or more of the first through fifth examples, the computing device is in communication with the medical device via a wired connection, and the computing device is included between the medical device and a hospital network. In a seventh example of the computing device optionally including one or more of the first through sixth examples, the medical device is a diagnostic imaging device, a medical therapy device, or a patient monitoring device.

In another embodiment, a method for servicing a medical device comprises encrypting a connection between a remote computing device and a supplemental computing device for a medical device, and converting between a first protocol used by the medical device and a second protocol used by the remote computing device to enable communication between the remote computing device and the medical device.

In a first example of the method, the method further comprises identifying the first protocol from a list of protocols. In a second example of the method optionally including the first example, the method further comprises blocking unverified traffic, the unverified traffic determined based on a set of screening rules. In a third example of the method optionally including one or more of the first and second examples, the method further comprises periodically querying the remote computing device to log into the medical device for servicing of the medical device.

In yet another embodiment, a system comprises a medical device, a remote computing device configured with executable instructions stored in non-transitory memory for servicing the medical device, and a supplemental computing device communicatively coupled to the medical device. The supplemental computing device includes executable instructions stored in non-transitory memory that when executed cause the computing device to: identify a first protocol used by the medical device, convert between the first protocol used by the medical device a second protocol used by the remote computing device, and encrypt communications with the remote computing device via a security protocol.

In a first example of the system, the system further comprises a hospital network, wherein the supplemental computing device and the medical device are included on the hospital network. In a second example of the system optionally including the first example, the system further comprises one or more external databases, the external databases included on the hospital network and in communication with the medical device and the supplemental computing device. In a third example of the system optionally including one or more of the first and second examples, the external databases include one or more of a picture archiving and communication system (PACS), hospital information system (HIS), a radiology information system (RIS), and an electronic medical record (EMR) system. In a fourth example of the system optionally including one or more of the first through third examples, the supplemental computing device comprises a firewall that blocks unverified traffic between the medical device and the hospital network and secures open ports on the medical device. In a fifth example of the system optionally including one or more of the first through fourth examples, the supplemental computing device does not block data from the one or more external databases. In a sixth example of the system optionally including one or more of the first through fifth examples, the supplemental computing device is an aftermarket device and is included between the medical device and the hospital network. In a seventh example of the system optionally including one or more of the first through sixth examples, the supplemental computing device is configured with additional executable instructions stored in non-transitory memory that when executed cause the computing device to identify one or more protocols used to communicate on the hospital network. In an eighth example of the system optionally including one or more of the first through seventh examples, the supplemental computing device is configured with additional executable instructions stored in non-transitory memory that when executed cause the computing device to identify itself to the remote computing device and periodically send a login request query to the remote computing device.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A supplemental computing device in communication with a medical device, a remote computing device, and one or more external databases, the supplemental computing device comprising:
non-transitory memory including executable instructions for:
selecting a first protocol for communicating with the medical device from among a plurality of possible protocols based on parameters of the medical device;
communicating information between the medical device and the remote computing device via the supplemental computing device, including: communicating the information between the supplemental computing device and the medical device via the first protocol, and communicating the information between the supplemental computing device and the remote computing device via an encrypted, second protocol;
communicating clinical data between the one or more external databases and the medical device; and
applying firewall screening rules, including categorizing incoming traffic as either verified or unverified traffic, and blocking unverified traffic and permitting verified traffic to pass through the supplemental computing device, where the incoming traffic includes the information communicated between the medical device and the remote computing device and the clinical data, and where the firewall screening rules are generated based on the parameters of the medical device; and
a processor for executing said executable instructions.

2. The computing device of claim 1, wherein the non-transitory memory further includes executable instructions for entering the parameters of the medical device into a look-up table stored in the non-transitory memory to select the first protocol, the look-up table including the plurality of possible protocols indexed by medical device parameters of a plurality of medical devices, and wherein the medical device and additional medical devices from the plurality of medical devices are coupled to the one or more external databases via a hospital network.

3. The computing device of claim 1, wherein the supplemental computing device is in communication with the medical device via a wired connection, and wherein the supplemental computing device is included between the medical device and a hospital network.

4. A method, executable by a supplemental computing device, for servicing a medical device in communication with the supplemental computing device, the method comprising:
encrypting a connection over the Internet between a remote computing device and the supplemental computing device;
converting, with the supplemental computing device, between a first protocol used by the medical device and a second protocol used by the remote computing device to enable communication between the remote computing device and the medical device via the supplemental computing device, where the supplemental computing device communicates with one or more external databases over a hospital network; and
blocking unverified traffic with the supplemental computing device and permitting verified traffic to pass through the supplemental computing device, the unverified traffic and the verified traffic determined based on a set of screening rules generated based on parameters of the medical device.

5. The method of claim 4, further comprising identifying the first protocol from a list of protocols based on the parameters of the medical device, and executing, via the supplemental computing device, a model on images received from the medical device.

6. The method of claim 4, further comprising periodically querying the remote computing device with the supplemental computing device to log into the medical device for servicing of the medical device.

7. A system, comprising:
a medical device included on a hospital network;
a remote computing device configured with executable instructions stored in non-transitory memory for servicing the medical device;
one or more external databases included on the hospital network and in communication with the medical device; and
a supplemental computing device communicates with the medical device and the one or more external databases via the hospital network and configured with executable instructions stored in non-transitory memory that when executed cause the supplemental computing device to:
identify a first protocol from a list of protocols based on parameters of the medical device;
executing a model on images received from the medical device;
convert between the first protocol used by the medical device a second protocol used by the remote computing device;
encrypt communications with the remote computing device via a security protocol;
apply a firewall to block, with the supplemental computing device, unverified traffic between the medical device and the hospital network, permit verified traffic to pass through the supplemental computing device, and secure open ports on the medical device, where the firewall does not block data from the one or more external databases, and where the unverified traffic and the verified traffic are determined based on a set of screening rules generated based on parameters of the medical device.

8. The system of claim 7, wherein the one or more external databases include one or more of a picture archiving and communication system (PACS), hospital information system (HIS), a radiology information system (RIS), and an electronic medical record (EMR) system.

9. The system of claim 7, wherein the supplemental computing device further identifies the verified traffic based on a protocol under which the verified traffic is sent.

10. The system of claim 7, wherein the supplemental computing device is an aftermarket device and is included between the medical device and the hospital network.

11. The system of claim 7, wherein the supplemental computing device is configured with additional executable instructions stored in non-transitory memory that when executed cause the computing device to identify one or more protocols used to communicate on the hospital network.

12. The system of claim 7, wherein the supplemental computing device is configured with additional executable instructions stored in non-transitory memory that when executed cause the supplemental computing device to identify itself to the remote computing device and periodically send a login request query to the remote computing device.

13. The computing device of claim 1, wherein generating the firewall screening rules based on the parameters of the medical device comprises generating the firewall screening rules based on one or more models of network protocols of the medical device stored on the supplemental computing device.

14. The computing device of claim 13, wherein selecting the first protocol for communicating with the medical device from among the plurality of possible protocols based on the parameters of the medical device comprises selecting the first protocol based on the one or more models of the network protocols.

* * * * *